United States Patent [19]

Wright

[11] Patent Number: 4,875,767

[45] Date of Patent: Oct. 24, 1989

[54] APPARATUS AND METHODS FOR MARKING THE VISUAL CENTER OF THE CORNEA OF A HUMAN EYE

[76] Inventor: Kenneth W. Wright, 1375 Pasqualito Dr., San Marino, Calif. 91108

[21] Appl. No.: 163,799

[22] Filed: Mar. 3, 1988

[51] Int. Cl.⁴ ............................ A61B 3/10; A61B 3/02
[52] U.S. Cl. .................................... 351/212; 351/205; 351/214; 351/223
[58] Field of Search ............... 351/205, 214, 221, 223, 351/212; 128/303.1, 316

[56] References Cited

U.S. PATENT DOCUMENTS

| | | |
|---|---|---|
| 1,510,114 | 9/1924 | Thorner . |
| 3,602,580 | 8/1971 | Samuels . |
| 4,165,744 | 8/1979 | Cravy et al. . |
| 4,357,079 | 11/1982 | Karasawa . |
| 4,417,579 | 11/1983 | Soloviev et al. . |
| 4,515,157 | 5/1985 | Fedorov et al. . |
| 4,648,400 | 3/1987 | Schneider et al. . |
| 4,678,297 | 7/1987 | Ishikawa et al. . |

Primary Examiner—Rodney B. Bovernick
Attorney, Agent, or Firm—Bright & Lorig

[57] ABSTRACT

An apparatus for identifying and marking the visual center of the cornea of a human eye includes a cylindrical tube for placement over the cornea of a human eye. The tube is open at one end and includes, inside the tube, a disk-shaped member having a central pinhole-sized opening near the open end of the tube. Farther from the open end of the tube are one or more illuminated disks having central pinhole-sized opacities, one in the shape of a ring, another in the shape of a dot. While a viewer focuses through the pinhole on these opacities, a movable member mounted coaxially with the tube is moved to engage and mark the central visual axis of the cornea.

14 Claims, 2 Drawing Sheets

APPARATUS AND METHODS FOR MARKING THE VISUAL CENTER OF THE CORNEA OF A HUMAN EYE

This invention relates to an apparatus for indentifying and marking the visual center of the córnea of a human eye. Accurately marking this visual center is an important aspect of refractive eye surgery. The apparatus includes cylindrical tube means, preferably having a circumference sufficiently large to substantially surround the cornera of a human eye. This tube is open at one end, and includes, inside the tube, sighting means for permitting a person looking into the device to align the fovea of his eye with the sighting means, and means movable along the axis of the tube means and the viewer's eye for marking the visual center on the corneal epithelium of the viewer's eye.

In preferred embodiments, the sighting means comprises an opaque, movable member, slidably mounted inside the tube, and having a small, central, pinhole-sized opening. This pinhole-sized opening provides means for focusing the viewer's eye on target means to achieve the desired alignment of the viewer's fovea with the visual axis of the viewer's eye despite refractive errors in the viewer's eye. In operation, this movable member is positioned in the tube near its open end, and relatively near to the eye of viewer. Also slidably mounted in the tube, farther away from its open end, is a second, preferably disk-shaped member having a central opacity or dot that lies on the same axis as the pinhole in the first member. Alternatively, the tube means may include two such slidable disk members having markers or sights in their centers with the markers aligned along the same axis of the tube. An alternative to the disk-shaped member having a central opacity or dot is a member having a centrally-positioned light-emitting diode (LED) or another eye-attracting means. More distant from the eye, and near the other end of the tube, is, optionally, light source means to illuminate the slidable member or members with the central opacity.

Mounted coaxially with the tube means, and preferably mounted inside the tube means, is means for marking the central visual axis on the corneal epithelium. Marking the cornea can be done with a dye or a semi-sharp marker that marks the corneal epithelium. This marking means is preferably movable along the longitudinal axis of the tube means, and is adapted to move upwardly and downwardly with respect to the tube means. In preferred embodiments, the marking means moves downwardly to engage the surface of the corneal epithelium, and upwardly to disengage from the same surface, while a viewer focuses on the central opacity on the slidable member or members inside the tube. The marking means can be round, square, rectangular, elliptical or other desired shape, and may include means for marking the cornea to facilitate surgery such as radial keratotomy. Alternatively, or in addition to the marking means, the tube means can include trefine means or other surgical cutting means, to perform a surgical operation on the eye.

This invention also relates to methods for marking the central visual axis of the cornea of a human eye comprising attracting the eye of a viewer through a pinhole to an illuminated opacity or opacities within a tube-shaped member or members so that the central visual axis of the cornea is coincident and coaxial with a marking apparatus, and marking this central visual axis on the viewer's cornea while the viewer focuses through the sighting device.

This invention can better be understood by reference to the drawings accompanying this disclosure, in which.

Figures 1, 2:
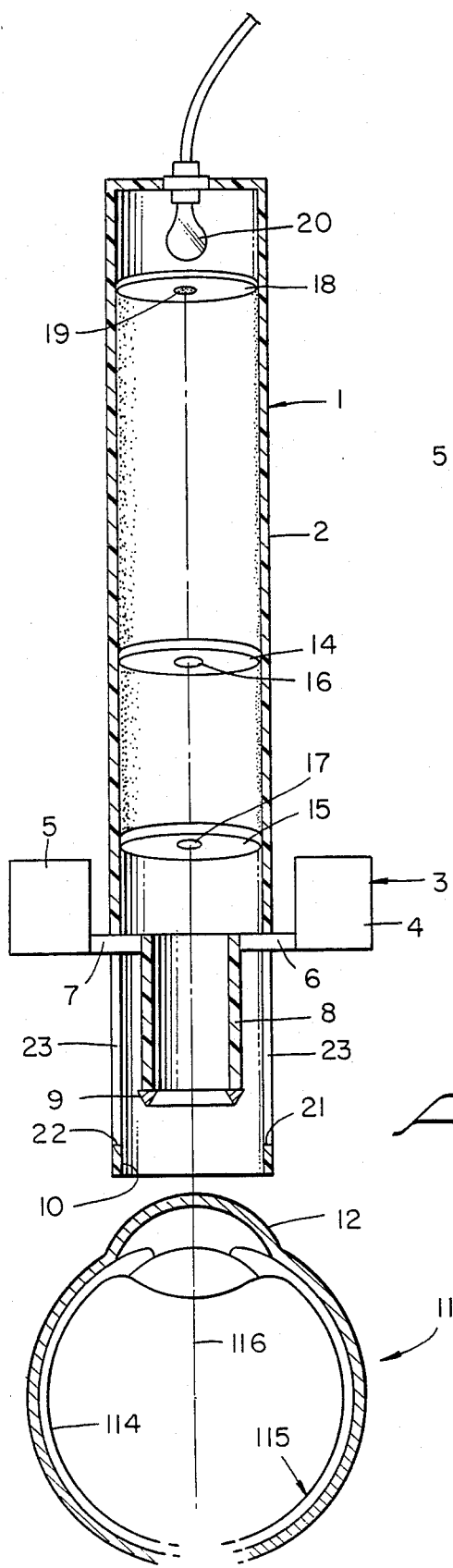
FIG. 1 shows a side elevation view, in cross-section, of a preferred embodiment of the new apparatus.
FIG. 2 shows an elevational view, in cross-section, of the corneal-marking means in the device depicted in FIG. 1.

FIG. 1 shows corneal-marking device 1 positioned in front of cornea 12 of human eye 11. Device 1 includes cylindrical tube member 2 having opening 10 just above the surface of cornea 12. Positioned inside tube 2 are slidable members 14 and 15 in the form of flat, round disks. Disk 14 has a center pinhole 16; disk 15, darkened ring 17. Also positioned inside tube 2 is slidable, flat, round disk 18 having darkened center spot 19. When the viewer focuses on dot 19 by looking through pinhole 16 and ring 17, he brings the fovea region 114 on retina 115 and the cornea visual axis 116 of eye 11 into coaxial alignment with the marking device. Light source 20 illuminates disk 18 and dot 19 to facilitate the viewer's focusing on dot 19. The light source is optional, because room light or operating microscope light may provide the needed illumination.

Figure 3A:
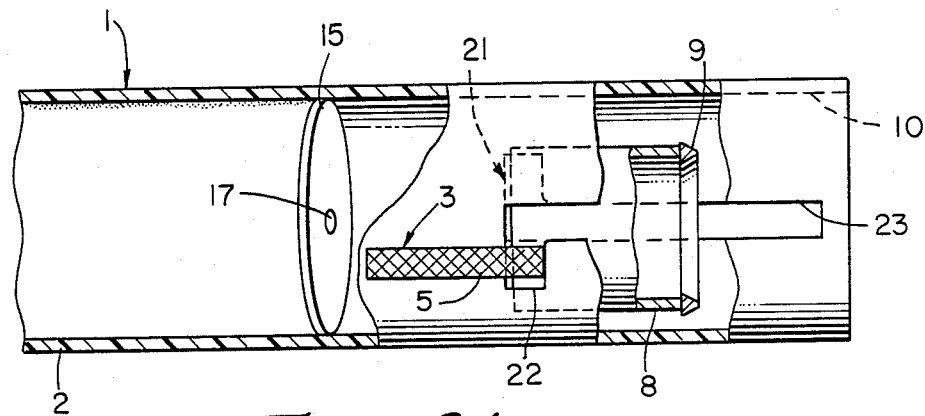
FIGS. 3A, 3B and 3C show the movement of the corneal-marking means from a locked position (FIG. 3A) to the unlocked position (FIG. 3B) and then into position to mark the cornea (FIG. 3C).
Figure 3B:
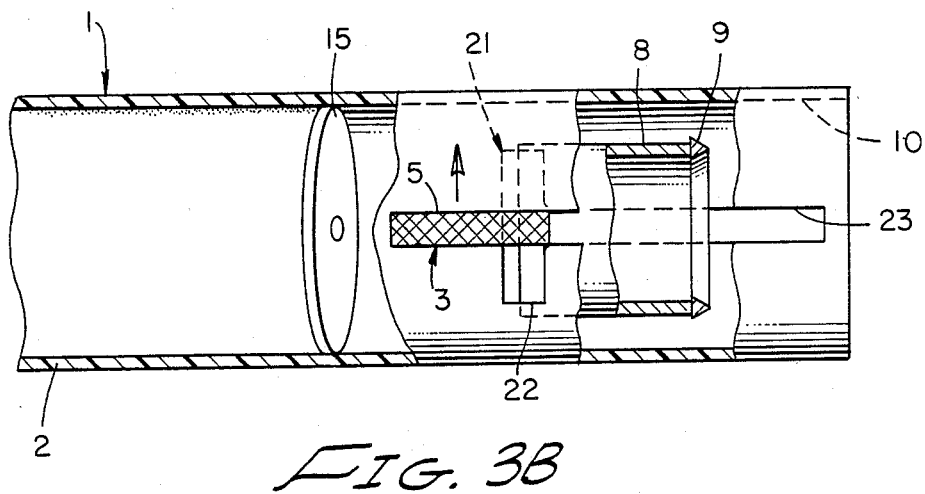
Figure 3C:
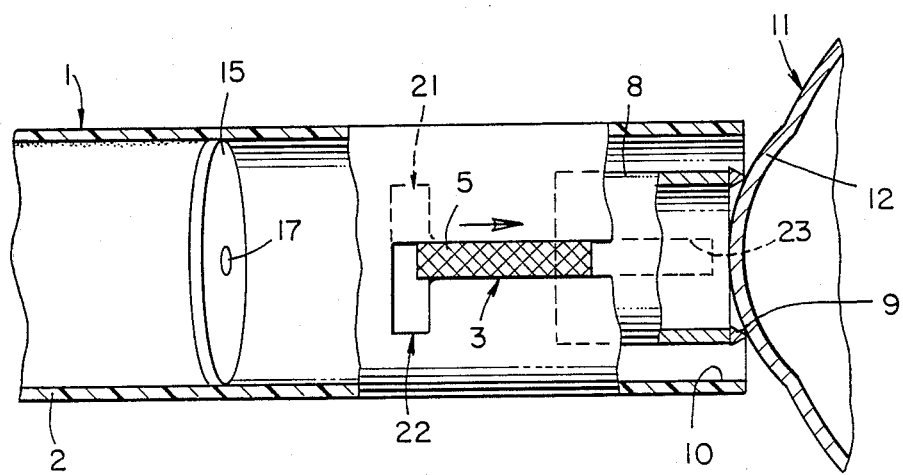

Corneal-marking member 3, as best seen in FIG. 2, includes corneal-marking ring 9 joined to cylinder 8. At or near the top of cylinder 8 are struts 6 and 7. Joined to struts 6 and 7 are finger tabs 4 and 5, respectively. Struts 6 and 7 project through the side wall of tube member 2 into L-shaped slots 21/22 located opposite one another on the walls of tube member 2 near opening 10. With strut 7 lying in the top of L-shaped slot 21/22, and strut 6 resting in a substantially similar slot on the opposite side of tube 2, corneal-marking ring 9 is held away from the surfaces of cornea 12. To mark the cornea, tab members 4 and 5 are moved to bring struts 7 and 6 into registry with long leg 21 of slots members 21/22 on opposite, facing sides of tube 2. Tab members 4 and 5 then permit the downward movement, as seen in FIG. 1, of tabs 4 and 5, struts 6 and 7 connected to tabs 4 and 5, ring 8 connected to struts 6 and 7, and corneal-marking ring 9, as seen in sequence in FIGS. 3A, 3B and 3C. Ring 9 marks the cornea by forming a circular depression on the cornea, or by inking the cornea with a transient, removable dye. In addition, ring 9 may include a surgical cutting tool to perform a surgical step on the eye.

In operation, a viewer looks into tube member 2, and focuses on opaque dot 19 through pinhole 16 and ring 17. By so doing, the viewer aligns his fovea and the central visual axis of his eye with the marking apparatus. With the viewer's eye focused on dot 19, corneal-marking ring 9 is lowered until ring 9 engages cornea 12, and places a circular mark cornea 12. The center of this circular mark on cornea 12 lies on the central visual axis of the eye, facilitating surgery that requires proper placement of a substitute cornea on this axis.

What is claimed is:

1. An apparatus for identifying and marking the visual center of a cornea of a user includes cylindrical tube means, said tube being open at one end, and having inside said tube, sighting means positioned for permitting said user looking into the device to align the fovea and visual axis of his eye with said sighting means, and means coaxial with said tube means for marking said visual center on the epithelium of said cornea.

2. The apparatus of claim 1 wherein said marking means comprises ring means adapted to move downwardly with respect to said tube means to engage and mark said visual center while a viewer focuses on said sighting means, and upwardly to disengage from said corneal epithelium.

3. The apparatus of claim 1 wherein said sighting means comprises a first opaque member mounted inside said tube means, said member having a small, central, pinhole-sized opening positioned near said open end, and a second member having a central opacity.

4. The apparatus of claim 2 wherein said sighting means comprises a first opaque member mounted inside said tube means, said member having a small, central, pinhole-sized opening positioned near said open end, and a second member having a central opacity.

5. A method for marking the visual axis of the cornea of a human eye of a user comprising attracting the eye of said user through a pinhole to an illuminated opacity within a tube-shaped member so that the visual axis of the cornea is coincident and coaxial with a marking apparatus, and marking said central visual axis while said user focuses on said opacity.

6. The method of claim 5 further comprising using as said illuminated opacity, means slidably mounted inside said tube-shaped member, said slidable means having a central opacity thereon.

7. The method of claim 5 further comprising using, as said illuminated opacity, two members slidably mounted inside said tube-shaped member, where one of said slidable members includes a centrally-located, darkened ring, and the other slidable member includes a centrally-located, darkened dot.

8. An apparatus for identifying and marking the line of sight at a user's cornea includes cylindrical tube means, said tube being open at one end, and having inside said tube, sighting means including at least two separate sights positioned for permitting said user looking into the device to align the apparatus coaxially with the line of sight of his eye with said sighting means, and means coaxial with said tube means for marking said visual center on the epithelium of said cornea.

9. The apparatus of claim 8 wherein said marking means comprises ring means adapted to move downwardly with respect to said tube means to engage and mark said visual center while said user focuses on said sighting means, and upwardly to disengage from said corneal epithelium.

10. The apparatus of claim 8 wherein said sighting means comprises a first opaque member mounted inside said tube means, said member having a small, central, pinhole-sized opening positioned near said open end, and a second member having a central opacity.

11. The apparatus of claim 9 wherein said sighting means comprises a first opaque member mounted inside said tube means, said member having a small, central, pinhole-sized opening positioned near said open end, and a second member having a central opacity.

12. A method for marking the line of sight of the cornea of a human eye of a user comprising attracting the eye of the user through a pinhole to an illuminated opacity within a tube-shaped member so that the line of sight of sight is coincident and coaxial with a marking apparatus, and marking said line of sight while said user views said opacity through said pinhole.

13. The method of claim 12 further comprising using as said illuminated opacity, means slidably mounted inside said tube-shaped member, said slidable means having a central opacity thereon.

14. The method of claim 12 further comprising using, as said illuminated opacity, two members slidably mounted inside said tube-shaped member, where one of said slidable member includes a centrally-located, darkened ring, and the ohter slidable member includes a centrally-located, darkened dot.

* * * * *